United States Patent
Sioshansi et al.

(10) Patent No.: US 6,217,615 B1
(45) Date of Patent: Apr. 17, 2001

(54) ARTHROPLASTY PROCESS FOR SECURELY ANCHORING PROSTHESES TO BONE, AND ARTHROPLASTY PRODUCTS THEREFOR

(75) Inventors: Piran Sioshansi, Lincoln; Raymond J. Bricault, Jr., West Boylston, both of MA (US)

(73) Assignee: Spire Corporation, Bedford, MA (US)

( * ) Notice: Subject to any disclaimer, the term of this patent is extended or adjusted under 35 U.S.C. 154(b) by 0 days.

(21) Appl. No.: 09/551,424

(22) Filed: Apr. 18, 2000

Related U.S. Application Data

(62) Division of application No. 08/932,361, filed on Sep. 16, 1997, now Pat. No. 6,051,751, which is a continuation of application No. 08/375,942, filed on Jan. 20, 1995, now abandoned.

(51) Int. Cl.$^7$ ............................. A61F 2/30; A61F 2/32; A61F 2/38; C23C 14/00
(52) U.S. Cl. .................................. 623/18.11; 623/20.14; 623/22.11; 623/23.6; 623/23.5; 427/523
(58) Field of Search ............................ 623/18.11, 20.14, 623/22.11, 23.5, 23.6; 427/523

(56) References Cited

U.S. PATENT DOCUMENTS

| | | | |
|---|---|---|---|
| 3,715,763 | 2/1973 | Link | 3/1 |
| 4,531,243 | 7/1985 | Weber et al. | 623/22 |
| 4,549,319 | 10/1985 | Meyer | 623/22 |
| 4,743,493 | 5/1988 | Sioshansi et al. | 428/217 |
| 5,133,757 | 7/1992 | Sioshansi et al. | 623/18 |
| 5,133,761 | 7/1992 | Krouskop | 623/21 |
| 5,236,509 | 8/1993 | Sioshansi et al. | 118/719 |
| 5,290,314 | 3/1994 | Koch et al. | 623/21 |
| 5,358,529 | 10/1994 | Davidson | 623/20 |
| 5,380,547 | 1/1995 | Higgins | 623/16 |
| 5,480,447 | 1/1996 | Skiba | 623/21 |

OTHER PUBLICATIONS

Edward M. Liston, "Using RF Plasma to Improve Potting and Coating" (Application Note—GaSonics Int'l Plasma Corp.).

Crystal G. Morris, "Plasma Treatment of Porous Polymer"s (Application Note—GaSonics Int'l Plasma Corp.).

Howmedica Int'l Ltd., "Surgical Simplex P Radiopaque Bone Cement" (1979).

Rointain F. Bunshah, et al., "Deposition Technologies for Films and Coatings", 170–173 (1982).

James K. Hirvonen, "Surface Modification of Polymers and Ceramics", Adv. Mater. & Processes Mag.—(May, 1986).

ASM International, "Engineered Materials Handbook", vol. 2, Engineering Plastics 169 (1988).

I.H. Loh et al., "Conducting Polymers by Ion Implantation", Nuclear Instr. & Methods in Physics Res. B34 (1988) pp. 337–346.

Edward M. Liston, "Plasma Treatment for Improved Bonding; A Review",; J. Adhesion, vol. 30 (1989), pp. 199–218.

E. Tobin et al., "Improved Surface Properties of Polymer Substrates by Ion Implantation", Soc. Of Plastics Engineers Conference Proceedings (1991), pp. 1111–1113.

(List continued on next page.)

Primary Examiner—Vincent Millin
Assistant Examiner—Choon P. Koh
(74) Attorney, Agent, or Firm—Thomas J. Engellenner; Nutter, McClennen & Fish, LLP

(57) ABSTRACT

A synovial prosthetic member includes a body having an articulating surface and an anchor surface, the articulating surface being configured for articulation with another articulating surface of a synovial joint, the anchor surface being configured for cementing to bone, the body being composed of ultrahigh molecular weight polyethylene (UHMWPE), the anchor surface having been subjected to treatment by either ion implantation, ion beam assisted deposition, or sputter deposition.

19 Claims, 6 Drawing Sheets

OTHER PUBLICATIONS

E.H. Lee et al., "Improved Surface Properties of Polymer Materials by Multiple Ion Beam Treatment", J. Mater, Res., vol. 6, No. 3 (Mar. 1991), pp. 610–628.

U.S. Dept. of Energy, Technology Transfer 92/93 (1992) pp. 113–114.

Campbell's Operative Orthapaedics (Eugenia A. Klein ed., Mosby Year Book, 1992), pp. 371–566, 627–664.

R. Schalek et al., "Low–Energy Ar$^+$Implantation of UHM-W–PE Fibers: Effect on Surface Energy, Chemistry, and Adhesion Characteristics," Mat. Res. Soc. Symp. Proc., vol. 236 (1992), pp. 335–340.

Jefferey P. Davies, et al., "The Effect of a Thin Coating of Polymethylmethacrylate on the Torsional Fatigue Strength of the Cement—Metal Interface", J. Applied Biomaterials, vol. 3 (1992), pp. 45–49.

E.H. Lee, et al., "Improved Hardness and Wear Properties of B–Ion Implanted Polycarbonate," J. –Mater. Res., vol. 7, No. 7. (Jul. 1992), pp. 1900–1911.

Don Paquin, "Surface Modification of Medical Polymers with Gas Plasma Technology", Polymed '93 Conf. Proc. (1993).

E.H. Lee et al., "Ion Beam Application for Improved Polymer Surface Properties", Nuclear Insruments and Methods in Physics Research B74 (1993), pp. 326–330.

J.D. Liao et al., "Adhesive, Wettable Surface Modifications of Polymers by Nitrogen Ion Implantation, Microwave Plasma, Gamma–Ray and Electron Beam Radiatons", Int'l Conf. On Polymers in Medicine & Surgery Proc. (1993).

E.H. Lee et al., "Hardness Measurements of Ar$^+$–Beam Treated Polyimide by Depth–Sensing Ultra Low–Load Indentation", J. Mater. Res., vol. 8, No. 2 (Feb. 1993), pp. 377–387.

Don Paquin, "Plasma Cleaning: An Alternative to Wet Chemicals", Engineers Digest (Jul. 1993).

E.H. Lee et al., "Effects of Electronic and Recoil Processes in Polymers During Ion Implantation", J. Mater.Res., vol. 9, No. 4 (Apr. 1994).

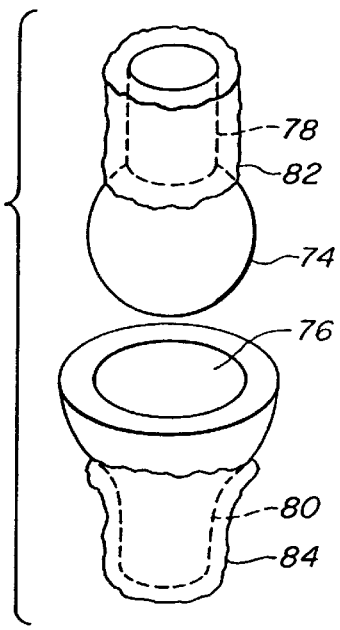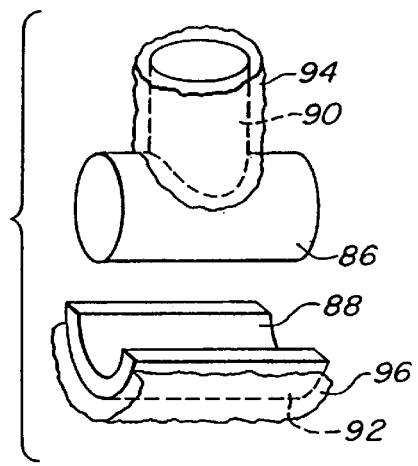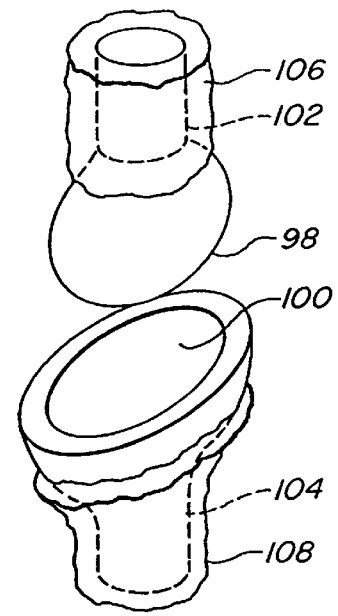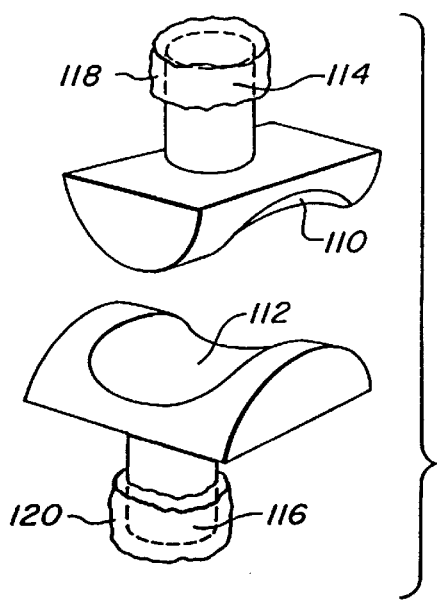
FIG. 2
FIG. 3
FIG. 4
FIG. 5

ARTHROPLASTY PROCESS FOR SECURELY ANCHORING PROSTHESES TO BONE, AND ARTHROPLASTY PRODUCTS THEREFOR

The current application is a division of commonly-owned, U.S. patent application Ser. No. 08/932,361, entitled "ARTHROPLASTY PROCESS FOR SECURELY ANCHORING PROSTHESES TO BONE AND ARTHROPLASTY PRODUCTS THEREFOR", filed on Sep. 16, 1997, now U.S. Pat. No. 6,051,751 which is a continuation of, and incorporates by reference, the commonly-owned U.S. patent application Ser. No. 08/375,942, filed on Jan. 20, 1995, now abandoned.

BACKGROUND OF THE INVENTION

1. Field of the Invention

The present invention relates to arthroplasty, i.e., an operation to restore motion between the bones of a skeletal joint, and concomitant function to muscles, ligaments and other tissue which control that joint. The present invention more particularly relates to cementing prostheses to bone.

2. The Prior Art

A prosthesis for a freely movable (synovial) skeletal joint comprises at least one member that has a configuration which presents an articulating surface and an anchor surface. The anchor surface is anchored to bone. The articulating surface bears against the corresponding articulating surface of another member.

In conventional hip, knee and like arthroplasties, for example, a member of a plastic or metal prosthesis is positioned with an anchor surface that is directly in contact with and mechanically anchored to bone either with or without cement. In the absence of cement, the integrity of the anchor typically relies upon the configuration of the anchor surface of the prosthesis member and intergrowth of bone and/or tissue with that surface. In the presence of cement, the integrity of the anchor typically relies, not only on adhesion, but also upon mechanical interlocking between (1) the cured cement, and (2) the adjoining or conjunctive anchor surfaces of the prosthesis member and the bone. Various problems have been encountered in implementing the above techniques.

Metal prostheses conventionally have been composed of either a titanium alloy or a cobalt-chromium alloy. Although these materials have advantages. in strength and surface integrity, they may suffer from problems that include less than desired in vivo performance. Plastic prostheses conventionally have been composed of ultra high molecular weight polyethylene (UHMWPE), and the cement therefor conventionally has been composed of polymethyl methacrylate (PMMA). These materials have excellent biocompatibility, but have suffered from poor adhesion to each other, as a result of which loosening occurs and debris is produced.

SUMMARY OF THE INVENTION

The present invention is based on the discovery that the adhesion between a high molecular weight polyene and an alkyl polyacrylate cement is radically improved if the surface of the polyene, prior to cementing, is predeterminedly modified by ion implantation, ion beam assisted deposition (IBAD), and/or sputter deposition.

The primary object of the present invention is to provide a prosthesis for a synovial joint, characterized by at least one polymeric member that has, (1) for anchoring to bone, an anchor surface that has been modified by ion implantation, ion beam assisted deposition, and/or sputter deposition, and (2) an articulating surface that is adapted to bear against the corresponding articulating surface of another member of the prosthesis member. The object of the present invention more specifically is to provide, in vivo, an assemblage comprising, in combination, such a prosthesis and a polymeric cement mantle interconnecting the anchor surface of the prosthesis and contiguous bone. The polymeric member contains a polyethylene with a molecular weight of greater than 200,000 as one of its characteristic ingredients, preferably an ultrahigh molecular weight polyethylene with a molecular weight ranging from $3 \times 10^6$ to $6 \times 10^6$. The cement contains an acrylic resin bonding agent/cement as one of its characteristic ingredients, preferably polymethyl methacrylate.

Preferably, in the case of ion implantation, an infusion of biocompatible ions is concentrated primarily in the outer 25 $\mu$m of the anchor surface. Preferably in the case of ion beam assisted deposition and sputter deposition, a coating of deposited material ranges in thickness from 2 to 5,000 nm. It is believed that the mechanism for enhanced adhesion in the case of ion implantation is an increased concentration of carbonyl groups, hydroxyl groups and/or three dimensional cross links, by which the surface becomes more hydrophilic. It is believed that the mechanism for enhanced adhesion in the case of IBAD and sputter deposition is the presence of inorganic atoms or molecules at the anchoring interface and the superior adhesion of the cement to those inorganic atoms or molecules.

BRIEF DESCRIPTION OF THE DRAWINGS

For a fuller understanding of the nature and objects of the present invention, reference is made to the following specification, which is to be taken in connection with the accompanying drawings, wherein:

FIG. 2 schematically illustrates a ball and socket prosthesis adapted for shoulder arthroplasty in accordance with the present invention;

FIG. 3 schematically illustrates a hinge joint prosthesis adapted for finger, elbow and knee arthroplasty in accordance with the present invention;

FIG. 4 schematically illustrates an ovoidal joint prosthesis adapted for wrist arthroplasty in accordance with the present invention;

FIG. 5 schematically illustrates a saddle joint prosthesis adapted for thumb joint arthroplasty in accordance with the present invention;

DETAILED DESCRIPTION OF THE PREFERRED EMBODIMENT

Figure 1:
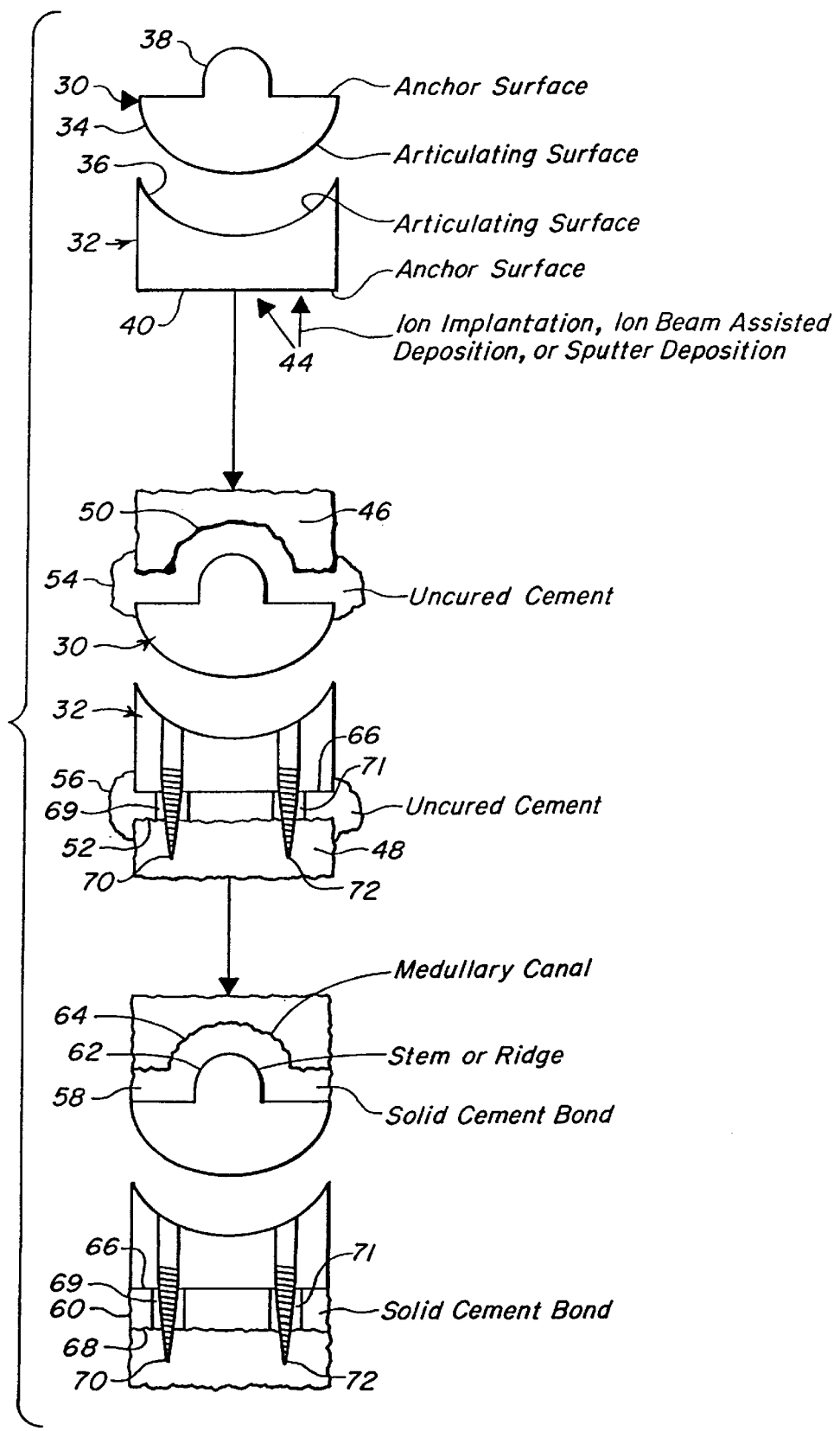
FIG. 1 is a flow diagram schematically illustrating a a process of the present invention and a product thereof.

The Flow Diagram of FIG. 1

FIG. 1 illustrates a pair of mating integral members 30, 32 of an artificial synovial joint. In the preferred embodiment, one member 30 is composed of metal or ceramic, and the other member 32 is composed of a high molecular weight polyene. Preferably, in a spherical joint, such as a hip joint, the metal or ceramic is a titanium alloy, a cobalt-chromium alloy, an alumina ceramic, or a zirconia ceramic. For all other joints, ceramic is not typically used and the metal is a titanium alloy or a cobalt-chromium alloy. Preferably, the high molecular weight polyene is an ultrahigh molecular weight polyethylene (UHMWPE). Members 30, 32 present contiguous articulating surfaces 34, 36 and remote conjunctive anchor surfaces 38, 40. Articulating surfaces 34, 36 have complementary configurations that constrain the members for movement under control of local muscles and with lubrication by synovial fluid.

As shown in FIG. 1, the present invention contemplates: modifying the anchor surface of the polymeric member 40 by ion implantation, ion beam assisted deposition (IBAD), or sputter deposition as at 44; matching configurations 38, 40 of the anchor surfaces with complementary surfaces 50, 52 of the bones 46, 48; interposing between the anchor surfaces and the complementary surfaces 50, 52 an uncured cement as at 54, 56; and, while the cement is curing, to provide solid bonds 58, 60, compressing the cement between each associated anchor surface 38, 40 and complementary surface 50, 52, and removing excess cement from the bone-prosthesis interfaces.

The metal member anchor surface 38 is shown as having a stem or ridge 62 which projects into a corresponding medullary canal 64 or trough in the bone 46 to which it is to become affixed. The polymeric member anchor surface 40 is shown as having a flat face 66 with protrusions 69, 71, and as being in close proximity with a corresponding flat face 68 of the bone 48 to which it is to become affixed, such that the ends of the protrusions 69, 71 are in contact with the bone 48. Metallic screws 70, 72 then connect member 32 to bone 48. The metallic screws 70, 72 may extend from the member 32 to the bone 48 by passing through the protrusions 69, 71, as in FIG. 1, or by bypassing the protrusions 69, 71. Cement 54, 56 initially is composed of a methyl acrylate polymerizate, and cures to cement mantles 58, 60 which are composed of polymethyl methacrylate (PMMA).

In an alternate embodiment, the metal member has a flat anchor face that is in contiguity with the corresponding flat face of the bone to which it is to become affixed, and the polymeric member has a stem or ridge which projects into a corresponding medullary canal or trough in the bone to which it is to become affixed.

In another alternate embodiment, both the metal member and the polymeric member have flat anchor faces that are in contiguity with the corresponding flat faces of the bones to which they are to become affixed.

In a further alternate embodiment, both the metal member and the polymeric member have stems or ridges which project into corresponding medullary canals or troughs in the bones to which they are to become affixed.

Ion Implantation of the Anchor Surfaces

As indicated above and in FIG. 1, one process of the present invention contemplates treating the polymeric member anchor surface 40, prior to cementing, by ion implantation as at 44. An applicable ion implantation process is disclosed in U.S. Pat. No. 5,133,757, issued Jul. 28, 1992 in the names of Piran Sioshansi and Richard W. Oliver, for "Ion Implantation of Plastic Orthopaedic Implants." The specification of U.S. Pat. No. 5,133,757 is incorporated hereinto by reference.

Preferably, ion implantation of one or both conjunctive surfaces involves exposure by an ion beam to a dose in the range of $1 \times 10^{13}$ to $5 \times 10^{17}$ ions/cm$^2$. Preferably, the ion beam is composed of gaseous or biocompatible ions selected from the class consisting of argon (Ar), boron (B), carbon (C), gold (Au), hafnium (Hf), helium (He), hydrogen (H), iridium (Ir), niobium (Nb), nitrogen (N), oxygen (O), palladium (Pd), platinum (Pt), silicon (Si), silver (Ag), tantalum (Ta), titanium (Ti), and zirconium (Zr). The energy of such an ion beam preferably ranges from 5 to 1,000 keV (thousand electron volts).

In practice, hydrogen atoms implanted as above are concentrated at the anchor surface in a zone that is at most 25 µm deep, and the other implanted ions are concentrated at the anchor surface in a zone that is at most 2 µm deep. The ion implanted zone in either case contains concentrations of carbonyl groups, hydroxyl groups and three-dimensional cross-links that are at least 10% greater than those groups and cross-links in the main body of the member below the ion implanted zone.

Ion Beam Assisted Deposition on the Anchor Surfaces

Alternatively, as indicated above and in FIG. 1, another process of the present invention contemplates treating the polymeric member anchor surface 40 by ion beam assisted deposition prior to cementing. An applicable ion beam assisted deposition process is disclosed in U.S. Pat. No. 5,236,509, issued Aug. 17, 1993 in the names of Piran Sioshansi and Raymond J. Bricault, Jr., for "Modular IBAD Apparatus for Continuous Coating." The specification of U.S. Pat. No. 5,236,509 is incorporated hereinto by reference.

Preferably, ion beam assisted deposition on one or both anchor surfaces involves simultaneous exposure in a vacuum to an ion source and an evaporation source, by which atoms from the evaporation source, in part, are driven into and onto the surface with assistance of the ion beam. The energy of the ion beam preferably is at least 50 eV (electron volts), generating an ion fluence of about 1 ion per 1,000 atoms being deposited and with a current density of about 45 microamps per cm$^2$.

Preferably, the ion beam is selected from the class consisting of hydrogen (H), helium (He), argon (Ar), nitrogen (N), and oxygen (O), and the atoms and molecules from the evaporation source are selected from the class consisting of biocompatible elements such as carbon (C), gold (Au), palladium (Pd), platinum (Pt), silicon (Si), silver (Ag), tantalum (Ta), titanium (Ti), and zirconium (Zr), and oxide and nitride ceramics of these elements. In practice, the resulting coating of such a deposit on the anchor surface ranges in thickness from 2 to 5,000 nm.

Sputter Deposition on the Anchor Surfaces

Alternatively, as indicated above and in FIG. 1, another process of the present invention contemplates treating the polymeric member anchor surface 40 by sputter deposition prior to cementing. Sputter deposition is a process by which a target material is bombarded by energetic particles, causing some of the target material to be ejected from the target and deposited onto the surface of the substrate, the material to be coated. Sputter deposition takes place in a vacuum, typically in the range of $1 \times 10^{-3}$ to $5 \times 10^{-7}$ Torr. The energetic particles are generally ions of a heavy inert gas, such as argon. In operation, the vacuum chamber in which the target and substrate are positioned is evacuated and then backfilled with the inert gas to a pressure of from 1 to 100 mTorr. The inert gas is subjected to an electrical charge, resulting in the gas being ionized in the vicinity of the target. The target is negatively charged, causing the positively charged ions to bombard its surface.

One typical sputter deposition apparatus is called a diode system. In this apparatus, the same electrical source is used to ionize the inert gas and to negatively charge the target. In the diode system, the electrical potential generally ranges from 200 to 5000 volts. When the target is an electrically conductive material, direct current can be used, and when the target is a non-electrically-conductive material, a radio frequency potential is applied to the target.

Preferably, the target material for sputter deposition is selected from the class consisting of biocompatible elements such as carbon (C), gold (Au), palladium (Pd), platinum (Pt), silicon (Si), silver (Ag), tantalum (Ta), titanium (Ti), and zirconium (Zr), and oxide and nitride ceramics of the these elements. In practice, the resulting coating of such a deposit on the anchor surface ranges in thickness from 2 to 5,000 nm.

Preferably, a radio frequency diode sputter deposition system is employed. The target is pure titanium and oxygen gas is mixed with the inert argon gas enabling the titanium and oxygen to combine to form titanium dioxide ($TiO_2$). The sputtering chamber is backfilled with argon and oxygen gasses at a ratio of 3:1 to a pressure of 1 mTorr. The deposition rate is 0.3 nm/sec and the thickness of the deposited titanium dioxide layer is 300 nm. The target voltage is 1000V.

The Synovial Joints of FIGS. 2 to 8

Figure 7:
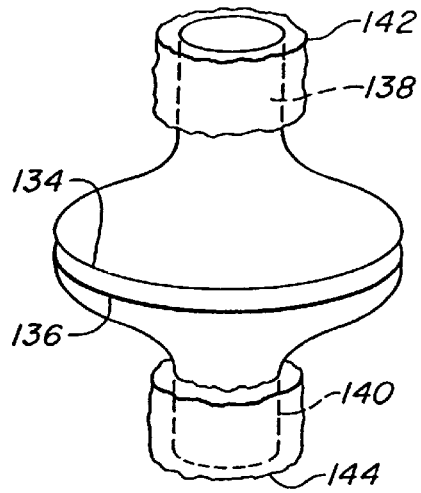
FIG. 7 schematically illustrates a gliding joint prosthesis adapted for carpus arthroplasty in accordance with the present invention.
Figure 6:
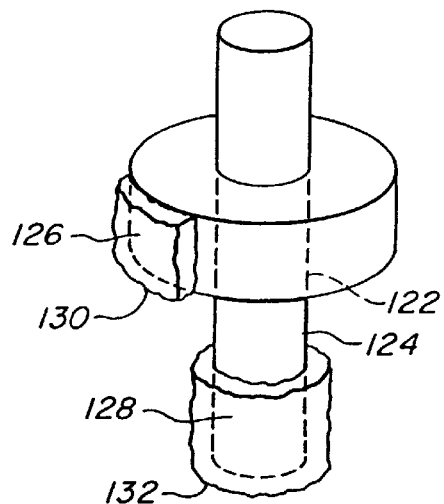
FIG. 6 schematically illustrates a pivot joint prosthesis adapted for forearm arthroplasty in accordance with the present invention.

The present invention is intended for application, in accordance with the present invention, to a wide variety of well known prosthetic joint configurations, of which FIGS. 2 to 8 are examples. All of the illustrated prosthetic joints incorporate (1) a ultrahigh molecular weight polyethylene member, the anchor surface of which has been exposed to ion implantation, ion beam assisted deposition, or sputter deposition, (2) a metal or ceramic member, and (3) polymethyl methacrylate mantles. FIG. 2 illustrates a hip or shoulder joint comprising ball and socket articulating surfaces 74, 76 anchor surfaces 78, 80, and cement mantles 82, 84, allowing angular movement in any direction. FIG. 3 illustrates a joint for fingers, elbows, and knees, comprising hinged articulating surfaces 86, 88, anchor surfaces 90, 92, and cement mantles 94, 96, allowing angular movement only in one plane. FIG. 4 illustrates a joint for wrists, comprising ovoid articulating surfaces 98, 100, anchor surfaces 102, 104, and cement mantles 106, 108, the articulating surfaces being ovoidal so that only angular movement, but not rotation, of one bone in relation to the other is possible. FIG. 5 illustrates a thumb joint comprising articulating saddle surfaces 110, 112, anchor surfaces 114, 116, and cement mantles 118, 120, allowing movement in two orthogonal directions. FIG. 6 illustrates a forearm joint, comprising pivotal articulating surfaces 122, 124, anchor surfaces 126, 128, and cement mantles 130, 132, such that one bone pivots about its own longitudinal axis. FIG. 7 illustrates a carpal joint, comprising articulating glide surfaces 134, 136, anchor surfaces 138, 140, and cement mantles 142, 144, characterized by two flat surfaces that allow sliding in any planar direction.

Figure 8:
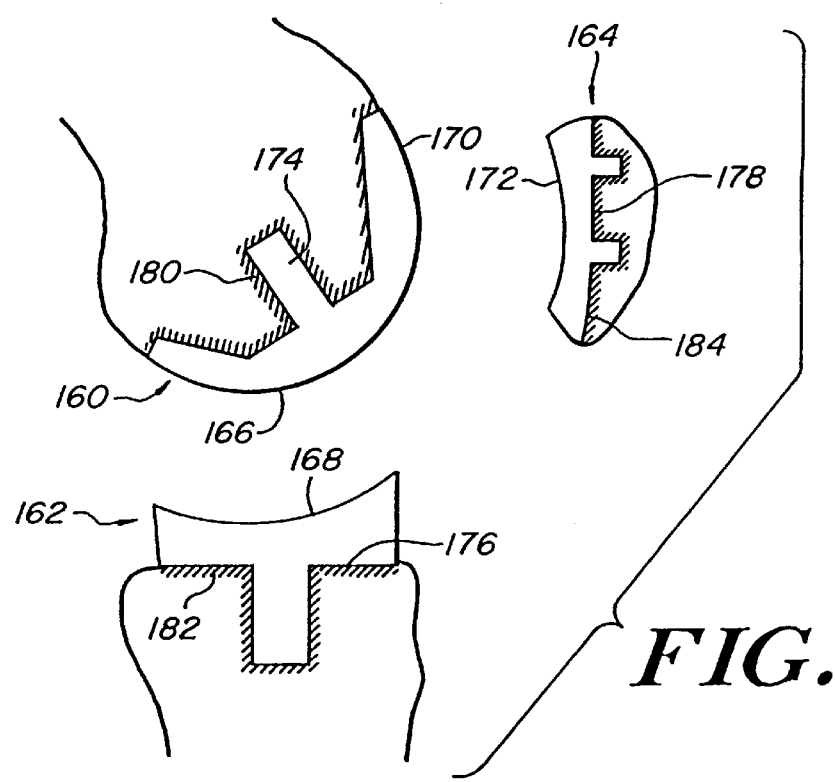
FIG. 8 schematically illustrates a complete knee joint prosthesis adapted in accordance with the present invention.

FIG. 8 illustrates a more complicated joint configuration for knees that includes a femur-tibia joint and a femur-patella joint. This configuration includes a femoral member 160, a tibial member 162, and a patellar member 164. Preferably, the femoral member 160 is metal and has two articulating surfaces 166, 170 and one anchor surface 174 with cement mantle 180. Preferably, the tibial member 162 is polymeric with one articulating surface 168 and one anchor surface 176 with cement mantle 182. Preferably, the patellar member 164 is polymeric with one articulating surface 172 and one anchor surface 178 with cement mantle 184. The femur-tibia joint is a hinge joint similar to the hinge joint described with reference to FIG. 3 and comprises articulating surfaces 166, 168. The femur-patella joint is a sliding joint comprising articulating surfaces 170, 172, wherein the patellar member articulating surface 172. slides vertically within the femoral member articulating surface 170.

In an alternative embodiment, the two femoral articulating surfaces 166, 170 are not discrete, but are contiguous.

EXAMPLE I - UHMWPE

The characteristics of UHMWPE polymer are outstanding abrasion resistance; among the highest impact resistance of any plastic material; low coefficient of friction; nonstick, self-lubricating surface; good chemical resistance; negligible water absorption; excellent energy absorption and sound-dampening properties; and excellent dielectric and insulating properties. This polymer does not melt, flow or liquify at its melting point of from 138 to 142° C. (280 to 289° F.), and retains excellent dimensional stability. Chemical resistance to aggressive media, including most strong oxidizing agents, is excellent. Exposure to aromatic and halogenated hydrocarbons results in only slight surface swelling if moderate temperature levels are maintained. The extremely high processing viscosities characteristic of its high molecular weight require special processing procedures because the polymer resin does not exhibit a measurable melt index. The most common methods for fabrication of UHMWPE are ram extrusion and compression molding. In both cases, individual UHMWPE particles are fused into what appears to be a solid, although microscopically they remain as discrete particles with segmented diffusion between them. Ram extrusion is accomplished by continuously feeding resin through a hopper into the extruder throat and then packing the material at infrequent intervals with a reciprocating plunger, thus removing the air phase. The compressed powder then moves through heated zones, where it is fused. The cross section of the barrel or die corresponds to the profile of the product. Production rates are influenced by the hydraulic system heater capacity, the die length, and the strength of the construction materials. Typical extrusion rates are 10 to 20 kg/h (22 to 44 lb/h). Controller set-point temperatures are 160 to 230° C. (320 to 446° F.).

Material properties are listed in Table 1 below.

TABLE I

| Property | Typical Values | Test Method |
| --- | --- | --- |
| Mechanical | | |
| Density, $g/cm^3$ | 0.926–0.934 | D 792 |
| Tensile strength at yield, MPa (ksi) | 21 (3.1) | D 638 |
| Tensile strength at break, MPa (ksi) | 48 (7.0) | D 638 |
| Elongation at break, % | 350 | D 638 |
| Young's modulus, GPa ($10^6$ psi) | | |
| At 23° C. (73° F.) | 0.69 (0.10) | D 638 |
| At −269° C. (−450° F.) | 2.97 (0.43) | D 638 |
| Izod impact strength, kJ/m (ft-lbf/in) notch | | |
| At 23° C. (73° F.) | 1.6 (30) | D 56(a) |
| At −40° C. (−40° F.) | 1.1 (21) | D 56(a) |
| Hardness, Shore D | 62–66 | D 2240 |
| Abrasion resistance | 100 | — |

TABLE I-continued

| Property | Typical Values | Test Method |
|---|---|---|
| Water absorption, % | Nil | D 570 |
| Relative solution viscosity, dl/g | 2.3–3.5 | D 4020 |
| Thermal | | |
| Crystalline melting range, powder, °C.(°F.) | 138–142(280–289) | Polarizing microscope |
| Coefficient of linear expansion, $10^{-4}$/K | | |
| At 20 to 100° C. (68 to 212° F.) | 2 | D 696 |
| At −200 to −100° C. (−330 to −150° F.) | 0.5 | D 696 |

TABLE I-continued

| Property | Typical Values | Test Method |
|---|---|---|
| Electrical | | |
| Volume resistivity, Ω-m | $>5 \times 10^{14}$ | D 257 |
| Dielectric strength, kV/cm (V/mil) | 900 (2300) | D 149 |
| Dielectric constant | 2.30 | D 150 |
| Dissipation factor, $\times 10^{-4}$ | | |
| At 50 Hz | 1.9 | D 150 |
| At 1 kHz | 0.5 | |
| At 0.1 MHz | 2.5 | |
| Surface resistivity, wt % carbon black, Ω | | |
| At 0.2% for color | $>10^{14}$ | D 257 |
| At 2.5% for UV protection | $10^{11}$ | D 257 |
| 6.5% for antistatic applications | $10^{5}$ | D 257 |
| 16.7% for conductive applications | $10^{3}$ | D 257 |

EXAMPLE II—PMMA

The cement of the present invention is sold by Howmedica under the trade designation SURGICAL SIMPLEX P RADIOPAQUE BONE CEMENT. This product initially is a mixture of polymethyl methacrylate monomer, methylmethacrylate styrene copolymer, and barium sulfate for radiopacity. Prior to use, the product is packaged in two sterile components. One component is an ampule containing 20 ml of a colorless, flammable liquid monomer which has a sweet, slightly acrid odor, and is of the following composition:

| Methyl methacrylate (monomer) | 97.4% v/v |
|---|---|
| N, N-dimethyl-p-toluidine | 2.6% v/v |
| Hydroquinone | 75 ± 15 ppm |

Formula: 
$$CH_2=C(CH_3)-COOCH_3$$

Hydroquinone is added to prevent premature polymerization which may occur under certain conditions, e.g., exposure to light and elevated temperatures. N, N dimethyl-p-toluidine is added to promote cold curing of the finished therapeutic compound. The liquid component is sterilized by membrane filtration.

The other component is a packet of 40 g of a finely divided white powder, a mixture of polymethyl methacrylate, methyl methacrylate styrene copolymer, and barium sulfate, as follows:

| Polymethyl methacrylate | 15.0% w/w |
|---|---|
| Methyl methacrylate styrene copolymer | 75.0% w/w |
| Barium sulfate | 10.0% w/w |

Formula:

$$CH_3-\underset{COOCH_3}{\underset{|}{\overset{CH_3}{\overset{|}{C}}}}-CH_2-\underset{COOCH_3}{\underset{|}{\overset{CH_3}{\overset{|}{C}}}}-CH_2-\underset{COOCH_3}{\underset{|}{\overset{CH_3}{\overset{|}{C}}}}\ldots \quad \ldots CH_2-\underset{COOCH_3}{\underset{|}{\overset{CH_3}{\overset{|}{C}}}}-CH_2-\underset{C_6H_3}{\underset{|}{CH}}-CH_2-\underset{COOCH_3}{\underset{|}{\overset{CH_3}{\overset{|}{C}}}}$$

The powder component is sterilized by gamma irradiation.

At the time of use, the powder and liquid are mixed, resulting in the exothermic polymeric formation of a soft, pliable, dough-like mass. Within a few minutes, as the reaction progresses, a hard, cement-like complex is formed. Upon completion of polymerization, the cement serves as a buffer for even weight distribution and other stresses between the prosthesis and bone. After application and during the completion of the polymerization process of the cement in situ, positioning of the prostheses is maintained securely without movement to obtain proper fixation. The completion of polymerization occurs in the patient and is an exothermic reaction with considerable liberation of heat. Temperatures occurring during the polymerization have been reported as high as 110° C.

Example III—Test Procedures

Figure 9:
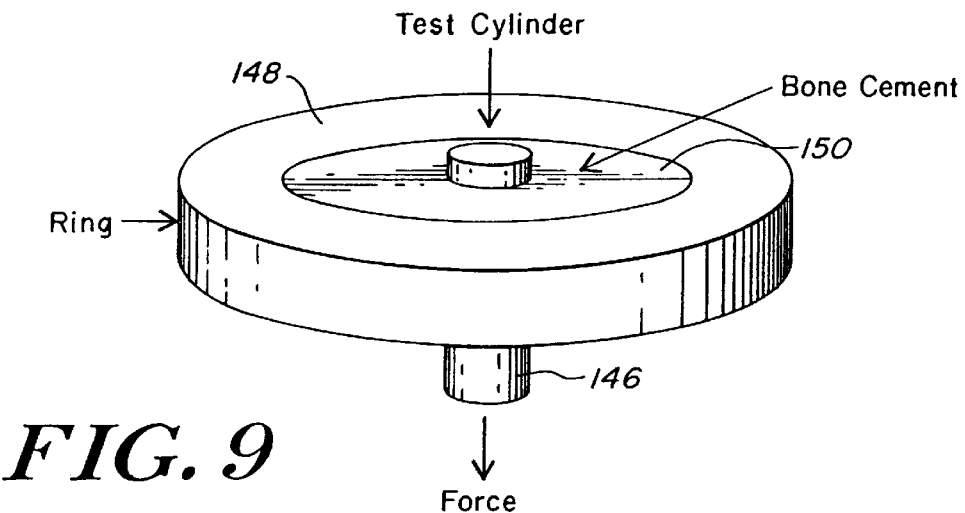
FIG. 9 illustrates a bone cement adhesion test procedure for evaluating test results in accordance with the present invention.
Figure 10:
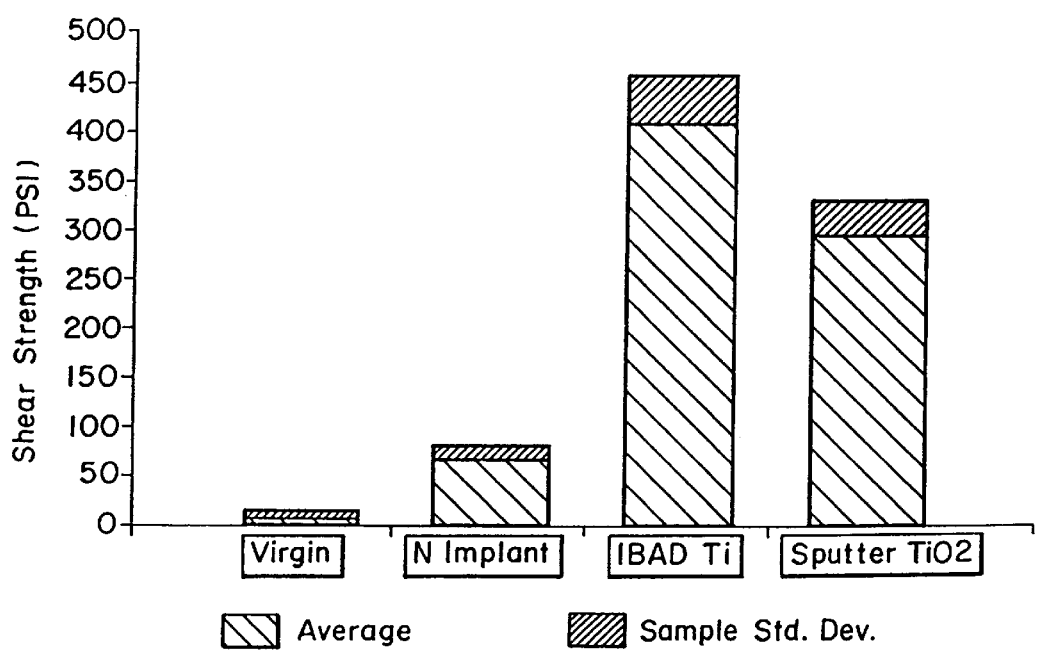
FIG. 10 graphically illustrates bone cement adhesion shear strength test results in accordance with the present invention.
Figure 11:
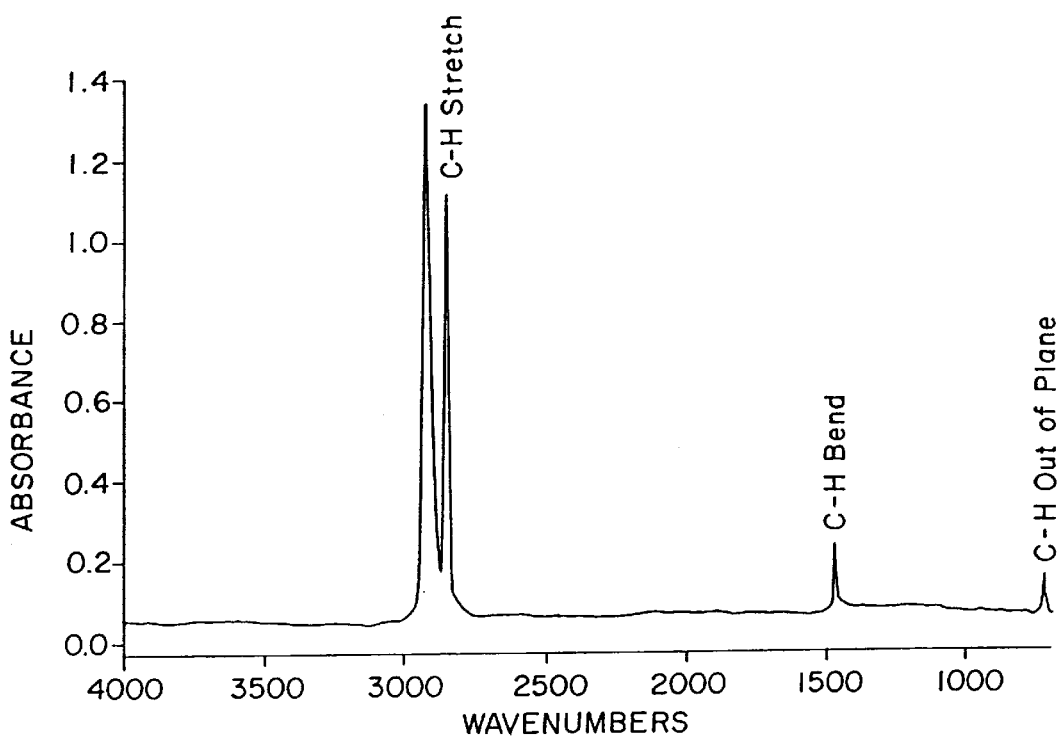
FIG. 11 illustrates a micro-FTIR spectrum of a UHMWPE control sample in accordance with the present invention.
Figure 12:
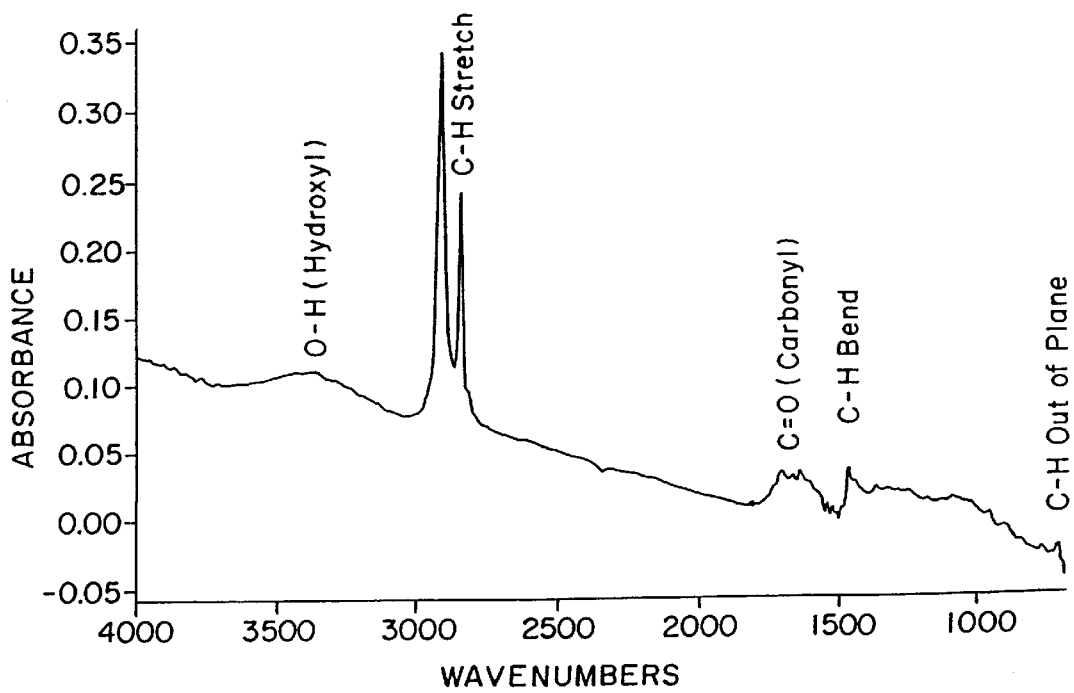
FIG. 12 illustrates a micro-FTIR spectrum of nitrogen ion implanted UHMWPE in accordance with the present invention.
Figure 13:
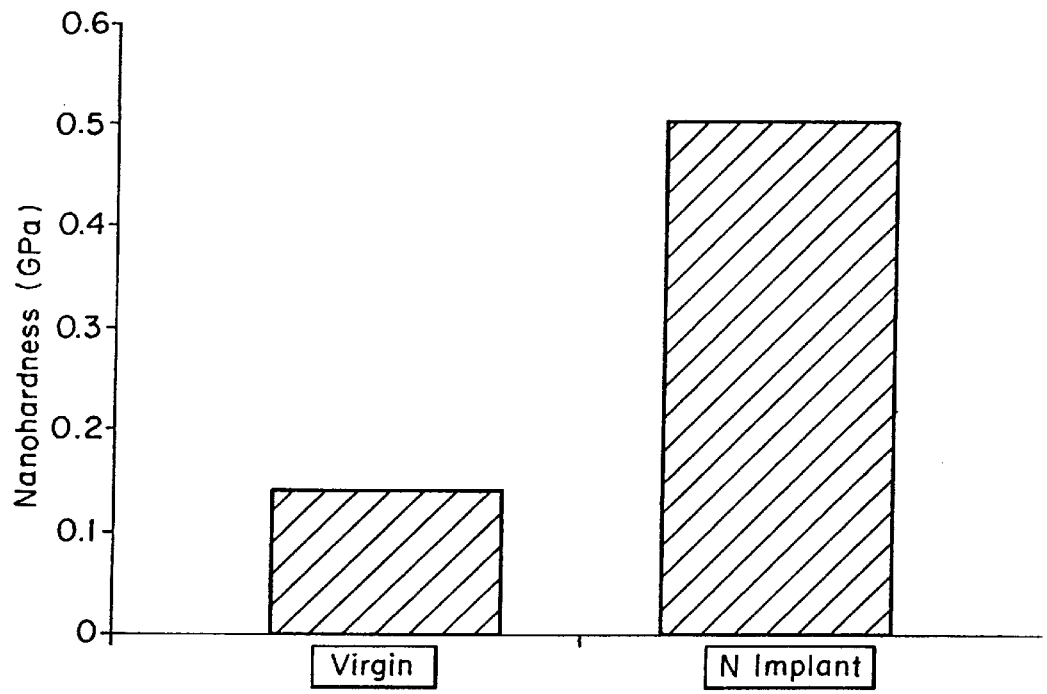
FIG. 13 shows nanohardness measurements of treated vs. untreated UHMWPE, illustrating certain principles of the present invention.
Figure 14:
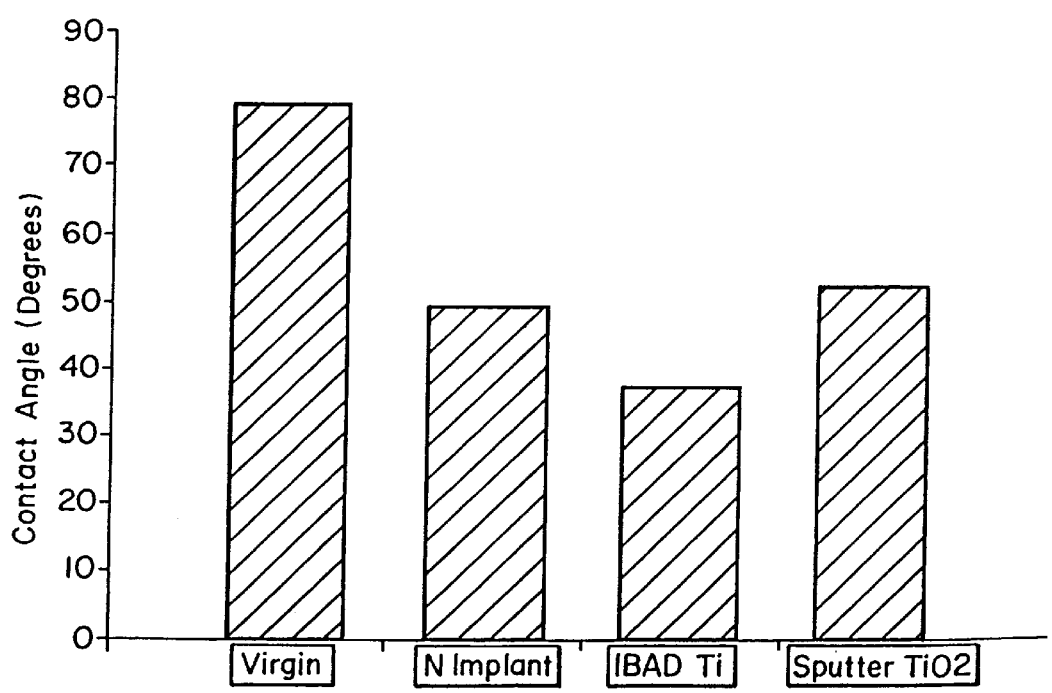
FIG. 14 shows water contact angle measurements of treated vs. untreated UHMWPE, illustrating certain principles of the present invention.

The test procedure illustrated in FIG. 9 demonstrates the advantages of the present invention as follows: Ten treated (test samples) and five untreated (control samples) UHMWPE cylinders, of the type shown at 146, are bonded axially within aluminum rings of the type shown at 148, by PMMA bone cement of the type shown at 150. The treated test samples are subjected to ion implantation, ion beam assisted deposition, or sputter deposition as discussed above. In the case of the ion implantation test samples, the anchor surfaces are exposed to a nitrogen ion beam to a dose of approximately $1 \times 10^{16}$ ions/cm$^2$ at an energy level of 140 keV. In the case of the IBAD test samples, titanium is deposited to a thickness of approximately 300 nm. In the case of the sputter deposition test samples, titanium dioxide is deposited to a thickness of approximately 300 nm. Shear tests of the cylinder-cement interfaces are performed by pulling the cylinders axially with respect to the rings. The forces necessary to remove the cylinders from the rings are depicted in FIG. 10, which shows that the adhesion shear strength is an order of magnitude greater for the treated cylinders than for the untreated cylinders. FIG. 11 illustrates a micro-FTIR spectrum a control sample and FIG. 12 illustrates a micro-FTIR spectrum of a test sample implanted with nitrogen. A comparison of these spectra indicates a high level of O—H (hydroxyl), C=O (carbonyl), and C—H (cross-linking) groups at the surfaces of the test samples relative to the surfaces of the control samples. FIG. 13 shows how much greater the nanohardness of the tests samples is relative to the control samples. FIG. 14 shows that the water contact angle of the test samples is lower relative to the control samples and, therefore, that the surfaces of the test samples are more hydrophilic than the surfaces of the control samples.

OPERATION

In operation, first the anchor surface of a prosthesis member is infused by ion implantation, coated by ion beam assisted deposition, or coated by sputter deposition. Next, the anchor surface is fitted to a complementary surface of bone, in the presence of a mixture of monomeric methyl methacrylate and a curing agent. Then curing occurs. The result is a synovial prosthetic member comprising a body having an articulating surface and an anchor surface, and a cement mantle by which the anchor surface is bonded to bone. This member thereby becomes a component of a synovial joint that is characterized by mated articulating surfaces.

What is claimed is:

1. A synovial prosthetic member which includes a bone-engaging surface having enhanced adhesion characteristics for cement comprising:
    a body having an articulating surface and bone-engaging surface;
    said articulating surface being configured for articulation with another articulating surface of a synovial joint;
    said anchor surface being configured for cementing to bone; and
    said anchor surface being characterized by subjection to treatment by a member of the class consisting of ion implantation, ion beam assisted deposition, and sputter deposition, such that said treated, bone-engaging surface of said prosthetic implant has enhanced adhesion characteristics for cement.

2. The apparatus of claim 1, wherein said prosthetic implant comprises a metal.

3. The apparatus of claim 2, wherein said metal is metal selected from the group consisting of titanium alloys and cobalt-chromium alloys.

4. The apparatus of claim 1, wherein said prosthetic implant comprises a ceramic.

5. The apparatus of claim 4, wherein said ceramic is a ceramic selected from the group consisting of alumina ceramic and zirconia ceramics.

6. The apparatus of claim 1, wherein said prosthetic implant comprises a polymer.

7. The apparatus of claim 6, wherein said polymer comprises a high molecular weight polyene.

8. The apparatus of claim 7, wherein said high molecular weight polyene comprises an ultrahigh molecular weight polyethylene (UHMWPE).

9. The apparatus of claim 8, wherein said UHMWPE has a molecular weight of greater than 200,000.

10. The apparatus of claim 9, wherein said UHMWPE has a molecular weight of between about $3 \times 10^6$ to about $6 \times 10^6$.

11. The apparatus of claim 1, wherein said treated bone-engaging surface is treated with at least one species of atoms selected from the group consisting of argon (Ar), boron (B), carbon (C), gold (Au), hafnium (Hf), helium (He), hydrogen (H), iridium (Ir), niobium (Nb), nitrogen (N), oxygen (O), palladium (Pd), platinum (Pt), silicon (Si), silver (Ag), tantalum (Ta), titanium (Ti), and zirconium (Zr).

12. The apparatus of claim 1, wherein said treated, bone-engaging, surface further comprises a surface which is coated with ions.

13. The apparatus of claim 12, wherein said treated, bone-engaging surface has a coating of ions with a thickness ranging from about 2 nm to about 5000 nm.

14. The apparatus of claim 1, wherein said treated, bone-engaging, surface further comprises a surface which is embedded with ions.

15. The apparatus of claim 14, wherein said treated, bone-engaging, surface has ions embedded to a depth between about 2 microns and about 25 microns.

16. The apparatus of claim 14, wherein said surface has dose of ions ranging from about $1 \times 10^{13}$ to about $5 \times 10^{17}$ ions/cm$^2$.

17. The apparatus of claim 1, wherein said implant is a polymeric implant and the treated bone-engaging surface further comprises a surface having an increased concentration of carbonyl groups.

18. The apparatus of claim 1, wherein said implant is a polymeric implant and the treated, bone-engaging surface further comprises a surface having an increased concentration of hydroxyl groups.

19. The apparatus of claim 1, wherein said implant is a polymeric implant and the treated, bone-engaging surface further comprises a surface having an increased level of cross-linking.

* * * * *